United States Patent [19]

Clubley et al.

[11] Patent Number: 5,294,371

[45] Date of Patent: Mar. 15, 1994

[54] CORROSION AND/OR SCALE INHIBITION

[75] Inventors: Brian G. Clubley, Wilmslow; Jan Rideout, Horwich, both of United Kingdom

[73] Assignee: FMC Corporation, Philadelphia, Pa.

[21] Appl. No.: 964,584

[22] Filed: Oct. 21, 1992

[30] Foreign Application Priority Data

Nov. 23, 1991 [GB] United Kingdom ............ 9125115

[51] Int. Cl.$^5$ .................................. C23F 11/16
[52] U.S. Cl. .................. 252/389.23; 252/180; 210/699; 422/15; 422/17; 562/24
[58] Field of Search ............ 252/180, 389.23; 210/699; 422/15, 17; 562/24

[56] References Cited

U.S. PATENT DOCUMENTS

| | | | |
|---|---|---|---|
| 4,029,577 | 6/1977 | Godlewski et al. | 210/58 |
| 4,374,733 | 2/1983 | Snyder et al. | 210/701 |
| 4,469,643 | 9/1984 | Tsuruoka et al. | 562/24 |
| 4,497,713 | 2/1985 | Geiger | 210/699 |
| 4,642,194 | 2/1987 | Johnson | 210/699 |
| 4,828,795 | 5/1989 | Cook et al. | 252/180 |

FOREIGN PATENT DOCUMENTS 0106114  9/1983  European Pat. Off.
2112370  7/1983  United Kingdom.

Primary Examiner—Robert L. Stoll
Assistant Examiner—Valerie Fee
Attorney, Agent, or Firm—Patrick C. Baker; Charles C. Fellows; Robert L. Andersen

[57] ABSTRACT

A corrosion- and/or scale inhibitor composition comprising: A) a corrosion- and/or scale inhibitor; and B) a compound having the formula (I):

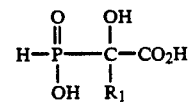

or a water-soluble salt thereof in which $R_1$ is hydrogen or methyl, the weight ratio of component A) to component B), ranging from 10:90 to 90:10.

The compounds of formula I are new compounds.

15 Claims, No Drawings

CORROSION AND/OR SCALE INHIBITION

The present invention relates to corrosion and/or scale inhibition and, in particular, to mixtures of corrosion and/or scale inhibitors for use in waters which optionally contain halogen or biocides which function by release of halogen.

One very effective group of corrosion and scale inhibitors for use in scale-forming industrial waters which are in contact with corrodable metals, especially ferrous metals, is that comprising hydroxy phosphonic acids. Notable amongst this group of acids 2-hydroxyphosphonoacetic acid, the use of which, as a corrosion inhibitor in water, is described and claimed in British Patent Specification No. 2112370. When used as inhibitors, however, in waters which contain halogen or biocides which release halogen, many inhibitors, including the hydroxy-phosphonic acid type, tend to suffer a reduction in their activity as corrosion and scale inhibitors.

This problem of loss of activity in chlorine-containing waters has been addressed previously, and one solution which has been offered, in U.S. Pat. No. 4,642,194, has been to treat the water with a specified water-soluble nitrogen-containing compound, preferably sulphamic acid. This approach, however, can result in the formation of halo-amines which are undesirable in that they are toxic and are unacceptable from the environmental view point. They also cause a reduction in the biocidal effect of the added halogen.

We have now found that when either or both of two new hydroxyphosphinocarboxylic acids is used in conjunction with a conventional corrosion and/or scale inhibitor, any chlorine-sensitivity of the conventional corrosion and/or scale inhibitor is greatly reduced and, moreover, the new hydroxyphosphinocarboxylic acid appears to provide a synergistic effect when used with conventional corrosion and/or scale inhibitors, even when used in essentially halogen-free aqueous environments.

Accordingly, the present invention provides a corrosion and/or scale inhibitor composition comprising:
A) a corrosion and/or scale inhibitor; and
B) a compound having the formula I:

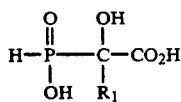

I in which R1 is hydrogen or methyl; or a water-soluble salt thereof, the weight ratio of component a) to component b) ranging from 10:90 to 90:10, preferably from 20:80 to 80:20.

Component A) of the inhibitor composition of the present invention may be, e.g. a phosphonocarboxylic acid having the formula II:

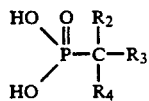

II or a water-soluble salt thereof, in which $R_2$ is $CO_2H$, $P(=O)(OH)_2$, $CH_2P(=O)(OH)_2$, $CH_2CH_2P(=O)(OH)_2$ or $NR_5R_6$ in which $R_5$ and $R_6$ are the same or different and each is, hydrogen-methyl, $C(R_7)_2P(=O)(OH)_2$ or $C(R_7)_2CO_2H$ in which $R_7$ is hydrogen or methyl; $R_3$ is hydrogen, $C_1-C_6$ alkyl, $CH_2CO_2H$ or $CH_2CH_2CO_2H$; and $R_4$ is hydrogen, hydroxyl, $CO_2H$, $P(=O)(OH)_2$, $CH_2CO_2H$ or $CH_2CH_2CO_2H$.

Preferably $R_2$ is $CO_2H$ or $P(=O)(OH)_2$; $R_3$ is hydrogen or methyl; and $R_4$ is hydroxyl.

Specific examples of compounds of formula II include:
phosphonoacetic acid
2-phosphonopropionic acid
2-phosphonoheptanoic acid
2-hydroxy phosphonoacetic acid
2-hydroxy-2-methyl phosphonoacetic acid
2-hydroxy-2-butyl phosphonoacetic acid
3-phosphono-3-hydroxy butyric acid
2-phosphonoethane-1,2-dicarboxylic acid
2-phosphono-butane-1,2,4-tricarboxylic acid
methane diphosphonic acid
1,2-ethanediphosphonic acid
1,3-propanediphosphonic acid
hydroxymethyl diphosphonic acid
hydroxyethyl diphosphonic acid (HEDP)
2-amino-phosphonoacetic acid
2-amino-2-methyl phosphonoacetic acid
nitrilo-tris-methylene phosphonic acid
methylamino-bis-methylene phosphonic acid
phosphonomethyl glycine
bis-phosphonomethyl glycine
phosphonomethylimino diacetic acid
1-aminoethyl-1,1-diphosphonic acid Water-soluble salts of compounds of formula II are, e.g., alkali metal salts, especially sodium or potassium salts; alkaline earth metal salts such as calcium or magnesium salts; ammonium salts; $C_1-C_8$ alkylamine salts such as methylamine, ethylamine, n-propylamine, trimethylamine, triethylamine, n-butylamine, n-hexylamine or n-octylamine salts; alkanolamine salts such as ethanolamine, di- or tri-ethanolamine salts; or heterocyclic amine salts such as morpholine salts.

Component A) of the inhibitor composition of the present invention may also be any of the other conventional corrosion and/or scale inhibitors, preferred examples of which include phosphates, e.g. sodium phosphate; aminoalkylenephosphonic acids such as aminotris(methylenephosphonic acid); and triazines such as those disclosed in European Patent Specification No. 46130, for example 2,4,6-tris(5'-carboxypentylamino)-1,3,5-triazine.

Component B) of the inhibitor composition of the present invention, viz, a compound of formula I, is a new compound and, as such, forms a further aspect of the present invention.

The compounds of formula I, per se, exhibit no corrosion or scale inhibition properties. It is very surprising, therefore, that when used in conjunction with known corrosion or scale inhibitors, they provide a corrosion and/or scale inhibiting composition which overcomes the longstanding chlorine sensitivity problem discussed above, as well as synergistic corrosion and/or scale inhibition when used in conjunction with conventional inhibitors in chlorine-free aqueous systems.

The compounds of formula I may be prepared by conventional methods namely by reacting sodium hypophosphite with glyoxylic acid or pyruvic acid, respectively. The respective reactions are conveniently conducted at an elevated temperature, e.g., at a temperature ranging from 60° to 110° C. in an aqueous reaction medium.

Water-soluble salts of the compounds of formula I may be of the same type as those illustrated hereinbefore in relation to the compounds of formula II.

Salts of the compounds of formula I or II, in which some or all of the acidic hydrogen atoms have been replaced by the respective cations, may be prepared by mixing an aqueous or alcoholic solution of the compound of formula I or II, with an aqueous or alcoholic solution containing an amount of the appropriate base in excess of, equal to or less than the stoichiometric requirement. The solvent may then be removed, e.g. by evaporation.

Many of the aqueous systems to be treated with a composition according to the present invention are sufficiently basic that the system itself is adequate to effect neutralisation of the acidic compound so that, when adding the acidic form of the compound of formula I or II, it is converted, in situ, into a metal salt form.

As already indicated, the inhibitor composition of the present invention provides excellent corrosion inhibition when incorporated into an aqueous system which is in contact with a corrodable metal surface, especially a ferrous metal, in particular iron. The inhibitor composition also imparts excellent scale inhibiting properties when incorporated into an aqueous system containing scale-forming salts, especially salts of calcium, magnesium, barium and strontium, especially calcium carbonate.

Accordingly, the present invention also provides a process for inhibiting corrosion—and/or scale in an aqueous system, comprising incorporating into the aqueous system, a corrosion—and/or scale inhibiting amount of a corrosion—and/or scale inhibiting composition comprising component A) and B), as hereinbefore defined.

In practice, the amount of the inhibitor composition which is added may vary, depending on the function, or functions, which the inhibitor composition is required to perform.

For corrosion-inhibiting protective treatments, optionally in combination with scale-inhibitor treatments, the amount of the inhibitor, composition added to the aqueous system conveniently ranges from 0.1 to 50,000 ppm (0.00001to 5% by weight), preferably from 1 to 500 ppm (0.0001 to 0.05% by weight), based on the weight of the aqueous system.

For solely anti-scale purposes, the amount of the inhibitor composition added conveniently ranges from 1 to 200 ppm, preferably from 1 to 30 ppm, based on the aqueous system.

The aqueous system which is treated according to the process of the present invention may be a totally aqueous or a partly aqueous medium.

Aqueous systems which may be effectively treated according to the present invention include e.g. cooling water systems, steam generating systems, sea-water evaporators, reverse osmosis equipment, bottle washing plants, paper manufacturing equipment, sugar evaporator equipment, soil irrigation systems, hydrostatic cookers, gas scrubbing systems, closed circuit heating systems, aqueous-based refrigeration systems, down-well systems, aqueous machining fluid formulations (e.g. for use in boring, milling, reaming, broaching, drawing, turning, cutting, sawing, grinding, and in thread-cutting operations, or in non-cutting shaping, spinning, drawing or rolling operations), aqueous scouring systems, aqueous glycol anti-freeze systems, water/glycol hydraulic fluids; and aqueous-based polymer surface coating systems.

The inhibitor compositions of the invention may be used in the process of the present invention either alone or in conjunction with other materials known to be useful in water treatment.

In the treatment of systems which are completely aqueous, e.g. cooling water systems, steam-generating systems, sea water evaporator systems, hydrostatic cookers and closed circuit heating systems, examples of further water treatment additives include one or more of further corrosion inhibitors; metal deactivators; further scale inhibitors/dispersing agents; threshold agents; precipitating agents; oxygen scavengers; sequestering agents; antifoaming agents; and biocides.

Further corrosion inhibitors which may be used, if they are not already present as component A) include water-soluble zinc salts; phosphates; polyphosphates; phosphonic acids or their salts; nitrates e.g. sodium nitrate; nitrites e.g. sodium nitrite; tungstates and molybdates e.g. sodium tungstate or molybdate; silicates e.g. sodium silicate; N-acylsarcosines; N-acylimino diacetic acids; ethanolamines; fatty amines; and polycarboxylic acids, e.g. polymaleic acid and polyacrylic acid (and their respective alkali metal salts), copolymers of maleic anhydride e.g. with sulphonated styrene, copolymers of acrylic acid e.g. with hydroxyalkylated acrylic acid, and substituted derivatives of polymaleic and polyacrylic acids and their copolymers.

Metal deactivators especially for copper, include benzotriazole, bisbenzotriazole or copper-deactivating derivatives of benzotriazole or tolutriazole, or their Mannich base derivatives, or mercaptobenzothiazole.

Scale inhibitors/dispersing agents include polymerized acrylic acid (or its salts), phosphine-polycarboxylic acids (e.g. those described in GB-PS 1458235), the cotelomers described in EP-PS 0150706, hydrolysed polyacrylonitrile, polymerized methacrylic acid and its salts, polyacrylamide and copolymers of acrylamide with acrylic and methacrylic acids, lignin sulphonic acid and its salts, tannin, naphthalene sulphonic acid/formaldehyde condensation products, starch and its derivatives, cellulose, acrylic acid/lower alkyl hydroxy-acrylate copolymers (e.g. those described in U.S. Pat. No. 4,029,577) styrene/maleic anhydride copolymers and sulphonated styrene homopolymers (e.g. those described in U.S. Pat. No. 4,374,733, and combinations of these).

Specific threshold agents, include hydrolysed polymaleic anhydride and its salts, alkyl phosphonic acids, and their salts, and alkali metal polyphosphates.

It will be clear from the above lists that certain additive compounds, e.g. phosphonocarboxylic acids, function both as scale inhibitors and as corrosion inhibitors.

Precipitating agent co-additives which may be used are alkali metal orthophosphates or carbonates; oxygen scavengers include alkali metal sulphites and hydrazines; sequestering agents are nitrilotriacetic acid and its salts; antifoaming agents are silicones, e.g. polydimethylsiloxanes, distearyl sebacamide, distearyl adipamide, and related products derived from ethylene oxide and/or propylene oxide condensations, in addition to fatty alcohols such as capryl alcohol and its ethylene oxide condensates. Biocides which may be used are, e.g. amines, quaternary ammonium compounds, m-chlorophenols, sulphur-containing compounds such as sulphones, methylene bis thiocyanates and carbonates, isothiazolines, brominated propionamides, triazines, phosphonium compounds, chlorine and chlorine-release agents, bromine and bromine release agents, and organometallic compounds such as tributyl tin oxide.

If the system to be treated according to the invention is not completely aqueous e.g. an aqueous machining fluid formulation, it may be e.g. a water dilutable cutting or grinding fluid.

The aqueous machining fluid formulations of the invention may be e.g. metal working formulations. By "metal working" we mean reaming, broaching, drawing, spinning, cutting, grinding, boring, milling, turning, sawing, non-cutting shaping or rolling. Examples of water-dilutable cutting or grinding fluids into which the inhibitor composition of the invention may be incorporated include:

a) Aqueous concentrates of one or more corrosion inhibitors, and optionally one or more anti-wear additives, used at dilutions of 1:50 to 1:100 which are usually employed as grinding fluids;

b) Polyglycols containing biocides, corrosion inhibitors and anti-wear additives which are used at dilutions of 1:20 to 1:40 cutting operations and 1:60 to 1:80 for grinding;

c) Semi-synthetic cutting fluids similar to b) but containing in addition 10 to 25% oil with sufficient emulsifier to render the water diluted product translucent;

d) An emulsifiable mineral oil concentrate containing, for example, emulsifiers, corrosion inhibitors, extreme pressure/anti-wear additives, biocides, antifoaming agents, coupling agents etc; they are generally diluted from 1:10 to 1:50 with water to a white opaque emulsion;

e) A product similar to d) containing less oil and more emulsifier which, on dilution to the range 1:50 to 1:100, gives a translucent emulsion for cutting or grinding operations.

Mixtures of sodium nitrite and triethanolamine have been used to inhibit corrosion in metal working but, because of related toxicity problems, due e.g. to the danger of forming N-nitrosamines, and because of legal regulations in some countries relating to effluents, alternatives to the use of sodium nitrite are being sought.

For those partly-aqueous systems in which the aqueous system component is an aqueous machining fluid formulation the inhibitor composition of the invention may be used singly, or in admixture with other additives e.g. known further corrosion inhibitors and/or extreme pressure additives.

Examples of other corrosion inhibitors which may be used in these aqueous systems, in addition to the inhibitor composition of the invention, include the following groups:

a) Organic acids, their esters or ammonium, amine, alkanolamine and metal salts, for example, benzoic acid, p-tert-butyl benzoic acid, disodium sebacate, triethanolamine laurate, iso-nonanoic acid, triethanolamine salt of (p-toluene sulphonamido caproic acid), sodium N-lauroyl sarcosinate or nonyl phenoxy acetic acid;

b) Nitrogen containing materials such as the following types: fatty acid alkanolamides; imidazolines, for example, 1-hydroxyethyl-2-oleyl-imidazolines; oxazolines; triazoles, for example, benzotriazoles, triethanolamines; fatty amines; and inorganic salts, for example sodium nitrate;

c) Phosphorus containing materials such as the following types: amine phosphates, phosphonic acids or inorganic salts, for example, sodium dihydrogen phosphate or zinc phosphate;

d) Sulphur containing compounds such as the following types: sodium, calcium or barium petroleum sulphonates, or heterocyclics, for example, sodium mercaptobenzothiazole.

Nitrogen containing materials, particularly triethanolamine, are preferred.

Examples of extreme pressure additives which may be present in the aqueous systems treated according to the present invention include sulphur and/or phosphorus and/or halogen containing materials, for instance, sulphurised sperm oil, sulphurised fats, tritolyl phosphate, chlorinated paraffins or ethoxylated phosphate esters.

When triethanolamine is present in the aqueous systems treated according to the present invention, it is preferably present in an amount such that the ratio of compound of formula I to triethanolamine is from 2:1 to 1:20.

The partly-aqueous systems treated by the process of the present invention may also be aqueous surface-coating compositions e.g. primer emulsion paints and aqueous powder coatings for metallic substrates.

The aqueous surface-coating composition may be e.g. a paint such as styrene-acrylic copolymer emulsion paint, a resin, latex, or other aqueous based polymer surface-coating systems.

Sodium nitrite and sodium benzoate have been used to inhibit flash rusting of aqueous based primer paints but, because of related toxicity problems and problems of emulsion stability at the high ionic concentrations used, industry is moving away from sodium nitrite and sodium benzoate.

In aqueous surface-coating compositions treated according to the invention the inhibitor composition of the present invention may be used singly, or in admixture with other additives e.g. known corrosion inhibitors, biocides, emulsifiers and/or pigments.

The further known corrosion inhibitors which may be used are e.g. those of classes a), b), c) and d) hereinbefore defined.

Examples of biocides which may be used in these aqueous systems, in addition to the compound of formula I, include the following:

Phenols and alkyl- and halogenated phenols, for example pentachlorophenol, o-phenyl phenol, o-phenoxyphenol and chlorinated o-phenoxyphenol, and salicylanilides, diamines, triazines and organometallic compounds such as organomercury compounds and organotin compounds.

Examples of pigments which may be used in these aqueous systems, in addition to the compound of formula I, include titanium dioxide, zinc chromate, iron oxide and organic pigments such as the phthalocyanines.

The following Examples further illustrate the present invention.

EXAMPLE 1

44 g of sodium hypophosphite, 37 g of glyoxylic acid (as its monosodium salt) and 500 mls of distilled water are charged into a reactor heated to a temperature of 102° C., under reflux conditions. The reaction is held at this reflux temperature and the progress of the reaction is monitored by $P^{31}$ NMR analysis. The reaction is stopped after 9 hours, at which point $^{31}P$ NMR analysis indicate the reaction mixture contained:

| | |
|---|---|
| 16.5% | PO₂ (sodium hypophosphite) |
| 74.0% | 2-hydroxyphosphinoacetic acid (sodium salt) |
| 5.0% | PO₃²⁻-ion |
| 4.5% | Phosphonic material (2-hydroxy phosphono acetic acid) |

The solids content of the reaction product is 13%

EXAMPLE 2

8.8 g. of sodium hypophosphite, 8.8 g of pyruvic acid and 50 g. of distilled water are charged into a reactor and heated to reflux, while stirring. The reaction mixture is held at the reflux temperature of 96° C., and the progress of the reaction is monitored by $^{31}$P NMR analysis.

After 11 hours, the reaction is stopped, at which point $^{31}$P NMR analysis indicated that the reaction mixture contained:

| | |
|---|---|
| 11.6% | PO₂ |
| 8.2% | PO₃²⁻-ion |
| 75.0% | 2-hydroxy-2-methylphosphinoacetic acid | the remainder being the di-addition product.

EXAMPLE 3

11 g. of sodium hypophosphite, 11.6 g. of glyoxylic acid (as its monosodium salt) and 30.1 g. of distilled water are charged into a reactor heated to a temperature of 75°–80° C. The reaction mixture is held at this temperature range, and the progress of the reaction is monitored by $^{31}$P NMR analysis. The reaction is stopped after 4.75 hours at which point $^{31}$P NMR analysis indicated that the reaction mixture contained:

| | |
|---|---|
| 11.1% | PO₂ |
| 72.0% | 2-hydroxyphosphinoacetic acid (as sodium salt) |
| 1.0% | PO₃²⁻-ion | the remainder being the di-addition product.

The solids content of the reaction product is 42.2% w/w.

EXAMPLE 4

Calcium carbonate (cooling water) threshold test

| Conditions | |
|---|---|
| Temperature | 70° C. |
| Test duration | 30 minutes |
| Aeration | — |
| Agitation | — |
| Calcium | 300 ppm as Ca²⁺ |
| Magnesium | 88 ppm as Mg²⁺ |
| Carbonate | 102 ppm as CO₃²⁻ |
| Bicarbonate | 538 ppm as HCO₃⁻ |
| Chlorine dosing | 5 ppm (as free Cl₂, delivered as NaOCl) |

This is a scale test in which the ability of an additive to inhibit CaCO₃ scale formation can be measured over a period of time. The test water used simulates the type of water found in a cooling water system. Likewise, the temperature of the test water represents a typical temperature close to heat exchangers in cooling water systems.

The severity of the test is increased by bubbling air and adding NaOCl to the system, and a constant mixture of particles in solution is enabled by agitating the test water.

A control experiment is conducted omitting the addition of NaOCl.

500 ml of solution, containing the above proportions of calcium chloride and magnesium chloride, are mixed with 500 mls of solution containing the above proportions of sodium carbonate and sodium bicarbonate, which already contains the additive under test. Air is bubbled through the resulting solution at-liters/minute, and the mixed solution is held at 70° C. for 30 minutes.

At the end of the 30 minute test period, a 50 mls sample is removed from each test solution. The sample is filtered under suction, and calcium remaining in the filtrate is determined by EDTA titration.

$$\% \text{ CaCO}_3 \text{ inhibition} = \frac{\text{titre of test} - \text{titre of blank}}{\text{titre of standard} - \text{titre of blank}} \times 100$$

The standard test solution comprises 500 mls containing 11.0 g./5 liters of CaCl₂.2H₂O and 7.50 g./5 liters of MgCl₂.6H₂O in 500 mls of the distilled water. The blank test solution contains 500 mls of the standard test solution and 500 mls of distilled water containing 1.80 g/5 liters Na₂CO₃ and 7.40 g/5 liters NaHCO₃.

The results are set out in Table I.

| | | | Percentage CaCO₃ inhibition | |
|---|---|---|---|---|
| Example | Test Additive | Dose Level ppm | Without chlorine | With chlorine |
| — | HEDP | 0.5 | 60 | 18 |
| — | Product Ex. 1 | 2.0 | 2 | 8 |
| 4 | HEDP: Product Ex. 1 | 0.5:2.0 | 65 | 63 |

It is clear that a mixture of HEDP and a compound of formula I provides a level of calcium carbonate scale inhibition, in waters containing chlorine, far greater than that achievable with the same amount of HEDP used above, despite the fact that the compound of formula I has very little inherent calcium carbonate scale inhibiting properties.

EXAMPLES 5 to 16

The corrosion inhibition performance of various inhibitor compositions of the present invention, are evaluated in the Rotating Coupon Test, using one or more of the following standard corrosive waters.

| | 50 Ca | 150 Ca | 300 Ca |
|---|---|---|---|
| PH | 7.0 | 8.5 | 8.3 |
| PA | 0 | 0 | 0 |
| TA | 20 | 350 | 300 |
| TH | 75 | 225 | 450 |
| CA²⁺ (ppm) | 50 | 150 | 300 |
| Mg²⁺ (ppm) | 25 | 75 | 150 |
| Cl⁻ (ppm) | 20 | 200 | 218 |
| SO₄²⁻ (ppm) | 200 | 200 | 38 |

In the above water compositions, PH denotes permanent hardness, PA denotes permanent alkalinity, TA denotes temporary alkalinity and TH denotes total hardness.

In a one liter reservoir of one of the test waters, two pre-cleaned and pre-weighed mild steel coupons are rotated at a coupon velocity of 61 cms per second. The test is conducted over 48 hours in oxygenated water at 40° C., using a specified amount of the corrosion inhibitor under test.

The coupons are removed, scrubbed without pumice, immersed for one minute in hydrochloric acid, inhibited with 1% by weight of hexamine, and then rinsed, dried and re-weighed. A certain loss in weight and a certain dimensional loss will have occurred. A blank (control) test, i.e. immersion of mild steel coupons in the test water in the absence of any test corrosion inhibitor is carried out in each series of tests. The corrosion rates are calculated in milligrams of weight loss/square decimeter/day (m.d.d.) and also in millimeters/year (m.p.y.).

The results are set out in Tables II and III. The results in Table II relate to tests carried out in water containing chlorine or a chlorine-producing agents, and those in Table III relate to tests conducted in water free from chlorine or chlorine-producing agents.

TABLE II

| Example | Test Additive | Concentration Additive (ppm) | Corrosion rate in test water | | | | | |
|---|---|---|---|---|---|---|---|---|
| | | | 50 Ca | | 150 Ca | | 300 Ca | |
| | | | m.d.d. | m.d.y | m.d.d. | m.p.y. | m.d.d. | m.p.y. |
| — | None | — | 358.9 | 68.0 | 186.9 | 35.5 | 67.3 | 12.8 |
| — | Product of Ex. 1 | 20 | 564.1 | 103.2 | 186.3 | 34.1 | 59.9 | 11.0 |
| — | Product of Ex. 2 | 20 | 292.9 | 53.6 | 94.2 | 17.2 | 56.1 | 10.3 |
| — | HPAA | 15 | 126.0 | 24.0 | 41.0 | 7.8 | 11.0 | 2.0 |
| — | HPAA free chlorine * | 15 30 | 317.0 | 60.2 | 51.0 | 9.7 | 24.0 | 4.0 |
| 5 | Product of Ext. 1 HPAA free chlorine | 20 15 30 | 216.6 | 39.6 | 19.0 | 3.5 | 13.3 | 2.4 |
| — | HEDP | 15 | 168.0 | 32.0 | 52.0 | 10.0 | 12.0 | 3.0 |
| — | HEPD free chlorine * | 15 30 | 304.0 | 56.0 | — | — | 24.0 | 4.0 |
| 6 | Product of Ex. 1 HEDP free chlorine * | 20 15 30 | 144.0 | 27.0 | 8.0 | 2.0 | 4.0 | 0.7 |
| — | PBSAM | 15 | 193.0 | 35.0 | — | — | 104.0 | 19.0 |
| — | PBSAM free chlorine * | 15 30 | 410.0 | 75.0 | — | — | 136.0 | 25.0 |
| 7 | Product of Ex. 1 PBSAM free chlorine * | 20 15 30 | 66.0 | 12.0 | — | — | 26.0 | 5.0 |
| — | Phosphate (Na₃PO₄.12H₂O) | 20 | — | — | 17.1 | 3.1 | — | — |
| — | Phosphate free chlorine * | 20 30 | — | — | 29.5 | 5.4 | — | — |
| 8 | Product of Ex. 1 phosphate free chlorine * | 20 20 30 | — | — | 14.3 | 2.6 | — | — |
| — | AMP | 15 | 232.0 | 66.0 | 118.0 | 22.0 | 11.0 | 2.0 |
| — | AMP free chlorine * | 15 30 | 358.0 | 66.0 | 26.0 | 5.0 | 16.0 | 3.0 |
| 9 | Product of Ex. 1 AMP free chlorine | 20 15 | 120.0 | 0.7 | 22.0 | 4.0 | 11.0 | 1.0 |
| — | TCPAT | 120 | 3.9 | 0.7 | — | — | — | — |
| — | TCPAT free chlorine * | 120 30 | 16.8 | 3.2 | — | — | — | — |
| 10 | Product of Ex. 1 TCPAT free chlorine * | 20 120 30 | 5.3 | 1.0 | — | — | — | — |
| — | HPAA | 15 | 126.0 | 24.0 | 41.0 | 7.8 | 11.0 | 2.0 |
| 11 | Product of Ex. 2 HPAA free chlorine * | 20 15 30 | 157.4 | 28.8 | 19.9 | 3.6 | 8.3 | 1.5 |

*present as NaOCl

TABLE III

| Example | Test Additive | Concentration Additive (ppm) | Corrosion rate in test water | | | | | |
|---|---|---|---|---|---|---|---|---|
| | | | 50 Ca | | 150 Ca | | 300 Ca | |
| | | | m.d.d. | m.d.y | m.d.d. | m.p.y. | m.d.d. | m.p.y. |
| — | None | — | 275.8 | — | 130.2 | — | — | — |
| — | Product of Ex. 1 | 20 | 564.1 | 103.2 | 186.3 | 34.1 | 59.9 | 11.0 |
| — | Product of Ex. 2 | 20 | 292.9 | 53.6 | 94.2 | 17.2 | 56.1 | 10.3 |
| — | HPAA | 15 | 126.0 | 24.0 | 41.0 | 7.8 | 11.0 | 2.0 |
| 12 | HPAA Product of Ex. 1 | 15 20 | — | — | 20.0 | 3.9 | — | — |
| — | HEDP | 15 | 168.0 | 32.0 | 52.0 | 10.0 | 12.0 | 3.0 |

TABLE III-continued

| Example | Test Additive | Concentration Additive (ppm) | Corrosion rate in test water | | | | | |
|---|---|---|---|---|---|---|---|---|
| | | | 50 Ca | | 150 Ca | | 300 Ca | |
| | | | m.d.d. | m.d.y | m.d.d. | m.p.y. | m.d.d. | m.p.y. |
| 13 | HEDP | 15 | 88.0 | 17.0 | 22.0 | 4.0 | 10.0 | 2.0 |
| | Product of Ex. 1 | 20 | | | | | | |
| — | PBSAM | 15 | 193.0 | 35.0 | 180.0 | 33.0 | 104.0 | 19.0 |
| 14 | PBSAM | 15 | 129.0 | 24.0 | 128.0 | 23.0 | 36.0 | 7.0 |
| | Product of Ex. 1 | | | | | | | |
| — | Phosphate (Na$_3$PO$_4$.12H$_2$O) | 20 | 213.5 | 39.1 | 17.1 | 3.1 | — | — |
| 15 | Phosphate | 20 | 51.0 | 9.3 | 11.4 | 2.1 | — | — |
| | Product of Ex. 1 | 20 | | | | | | |
| — | AMP | — | 232.0 | 66.0 | — | — | 11.0 | 2.0 |
| 16 | AMP | 15 | 78.0 | 14.0 | — | — | 9.0 | 2.0 |
| | Product of Ex. 1 | 20 | | | | | | |

In each of Example 12 to 16, the corrosion inhibiting effect of a compound of formula I with, the relevant known corrosion inhibitor, is much greater than that achieved with the respective known corrosion inhibitor used alone.

In Table II, HPAA denotes 2-hydroxyphosphonoacetic acid; HEDP denotes hydroxyethyl diphosphonic acid; PBSAM denotes 2-phosphonobutane-1,2,4-tricarboxylic acid; AMP denotes aminotrisphosphonic acid; and TCPAT denotes 2,4,6-tris(5'-carboxypentylamino)-1,3,5-triazine.

In each of Examples 5 to 11, the combination of a compound of formula I and a conventional corrosion inhibitor gave a corrosion inhibiting performance in chlorine-containing water, which is greatly improved relative to the use of the corrosion inhibitor alone, despite the fact that neither compound of formula I had any useful inherent corrosion inhibiting properties.

We claim:

1. A corrosion- and/or scale inhibitor composition comprising: A) a corrosion- and/or scale inhibitor; and B) a compound having the formula (I):

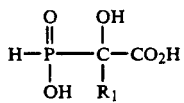

or a water-soluble salt thereof, in which $R_1$ is hydrogen or methyl the weight ratio of component A) to component B) ranging from 10:90 to 90:10.

2. A composition according to claim 1 in which the weight ratio of component A) to component B) ranges from 20:80 to 80:20.

3. A composition according to claim 2 in which the weight ratio of component A) to component B) ranges from 40:60 to 60:40.

4. A composition according to claim 1 in which component A) is a phosphonocarboxylic acid having the formula II:

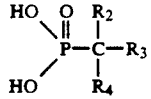

or a water-soluble salt thereof, in which $R_2$ is $CO_2H$, $P(=O)(OH)_2$, $CH_2P(=O)(OH)_2$, $CH_2CH_2P(=O)(OH)_2$ or $NR_5R_6$ in which $R_5$ and $R_6$ are the same or different and each is $C(R_7)_2 P(=O)(OH)_2$ or $C(R_7)_2 CO_2H$ in which $R_7$ is hydrogen or methyl; $R_3$ is hydrogen, $C_1$-$C_6$ alkyl, $CH_2CO_2H$ or $CH_2CH_2CO_2H$; and $R_4$ is hydrogen, hydroxyl, $CO_2H$, $P(=O)(OH)_2$, $CH_2CO_2H$ or $CH_2CH_2CO_2H$.

5. A composition according to claim 4 in which $R_2$ is $CO_2H$ or $P(=O)(OH)_2$; $R_3$ is hydrogen; and $R_4$ is hydroxyl.

6. A composition according to claim 4 in which the compound of formula II is
phosphonoacetic acid,
2-phosphonopropionic acid,
2-phosphonoheptanoic acid,
2-hydroxy phosphonoacetic acid,
2-hydroxy-2-methyl phosphonoacetic acid,
2-hydroxy-2-butyl phosphonoacetic acid,
3-phosphono-3-hydroxy butyric acid,
2-phosphonoethane-1,2-dicarboxylic acid,
2-phosphono-butane-1,2,4-tricarboxylic acid,
methane diphosphonic acid,
1,2-ethanediphosphonic acid,
1,3-propanediphosphonic acid,
hydroxymethyl diphosphonic acid,
hydroxyethyl diphosphonic acid (HEDP),
2-amino-phosphonoacetic acid,
2-amino-2-methyl phosphonoacetic acid,
nitrilo-tris-methylene phosphonic acid,
methylamino-bis-methylene phosphonic acid,
phosphonomethyl glycine,
bis-phosphonomethyl glycine,
phosphonomethylimino diacetic acid or
aminoethyl-1,1-diphosphonic acid.

7. A composition according to claim 1 in which component A) is a phosphate, an aminopolyphosphonic acid or a triazine.

8. A composition according to claim 7 in which the phosphate is sodium phosphate, the aminopolyphosphonic acid is amino tris(phosphonic acid) and the triazine is 2,4,6-tris(5'-carboxypentylamino)-1,3,5-triazine.

9. A process for inhibiting corrosion and/or scale in an aqueous system comprising incorporating into the aqueous system a corrosion- and/or scale inhibiting amount of an inhibitor composition as claimed in any one of claims 1 to 8.

10. A process according to claim 9 in which the inhibitor composition is added in an amount of from 0.1 to 50,000 ppm based on the weight of the aqueous system.

11. A process according to claim 10 in which the inhibitor composition is added in an amount from 1 to 500 ppm based on the weight of the aqueous system.

12. A process according to claim 9 in which the aqueous system treated is that comprised in a cooling water system, a steam generating system, a sea water evaporator, reverse osmosis equipment, bottle washing plants, paper manufacturing equipment, sugar evaporator equipment, soil irrigation systems, hydrostatic cookers, gas scrubbing systems, closed circuit heating systems, aqueous-based refrigeration systems, down-well systems, aqueous machining fluid formulations, aqueous scouring systems, aqueous glycol anti-freeze systems, water/glycol hydraulic fluids or aqueous-based polymer surface coating systems.

13. A process according to claim 9 in which the inhibitor composition is used in conjunction with one or more further corrosion inhibitors, metal deactivators, scale inhibitors/dispersing agents, threshold agents, precipitating agents, oxygen scavengers, sequestering agents, anti-foaming agents, and biocides.

14. A process according to claim 9 in which the aqueous system contains chlorine or a chlorine-producing agent.

15. A compound having the formula I

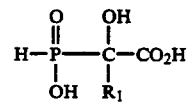

or a water-soluble salt thereof, in which R is hydrogen or methyl.

* * * * *